United States Patent [19]

Asamori et al.

[11] Patent Number: 6,013,681

[45] Date of Patent: Jan. 11, 2000

[54] PRODUCTION OF BITUMINOUS EMULSION AND LIQUID AMINE EMULSIFIER THEREFOR

[75] Inventors: Katsuhiko Asamori; Ryoichi Tamaki; Hitoshi Funada; Takao Taniguchi, all of Wakayama, Japan; Francisco Castañeda Juárez, Jalisco, Mexico; César Alvarez Ortiz, Jalisco, Mexico; Alvaro Gutiérrez Muñiz, Jalisco, Mexico; Humberto Ramirez Hernández, Jalisco, Mexico

[73] Assignee: Kao Corporation, Tokyo, Japan

[21] Appl. No.: 09/029,015

[22] PCT Filed: Oct. 6, 1996

[86] PCT No.: PCT/JP96/02881

§ 371 Date: Feb. 17, 1998

§ 102(e) Date: Feb. 17, 1998

[87] PCT Pub. No.: WO97/13808

PCT Pub. Date: Apr. 17, 1997

[30] Foreign Application Priority Data

Oct. 9, 1995 [JP] Japan ..................................... 7-261708
May 30, 1996 [JP] Japan ..................................... 8-136422

[51] Int. Cl.⁷ .............................. B01J 13/00; C08L 95/00
[52] U.S. Cl. .............................. 516/43; 106/277; 564/473
[58] Field of Search .............................. 516/43; 106/277; 564/473

[56] References Cited

U.S. PATENT DOCUMENTS

| | | | |
|---|---|---|---|
| 2,314,242 | 3/1943 | Porter, Jr. | 106/277 X |
| 3,340,203 | 9/1967 | Ferm | 516/43 X |
| 3,651,000 | 3/1972 | Woodruff | 516/43 X |
| 3,975,295 | 8/1976 | Koch | 516/43 X |
| 4,172,046 | 10/1979 | Doi et al. | 516/43 |
| 4,561,900 | 12/1985 | Brouard et al. | 106/246 |
| 4,701,484 | 10/1987 | Chang et al. | 524/59 |
| 4,976,784 | 12/1990 | Schilling | 106/277 |
| 4,997,481 | 3/1991 | Schilling | 106/277 |
| 5,160,453 | 11/1992 | Schilling | 252/311.5 |

FOREIGN PATENT DOCUMENTS 0340054 11/1989 European Pat. Off. .
1462981 5/1965 France .

*Primary Examiner*—Richard D. Lovering
*Attorney, Agent, or Firm*—Birch, Stewart, Kolasch & Birch, LLP

[57] ABSTRACT

A liquid amine compound which can be applied to various uses such as emulsification for bitumens since it has as high surface activity as those of solid amines and is more excellent in workability as compared with the solid amines, and an emulsifier for bitumens produced by using the amine compound. Furthermore, a process for producing an emulsifier a bituminous emulsion by reacting an aliphatic amine having at least one hydrocarbon group having not less than 8 carbon atoms with a carbonyl compound and adding an acid thereto to adjust the pH of the amine compound so as to be not more than 5, and a process for producing a bituminous emulsion composition by using the amine compound.

19 Claims, 3 Drawing Sheets

FIG.3
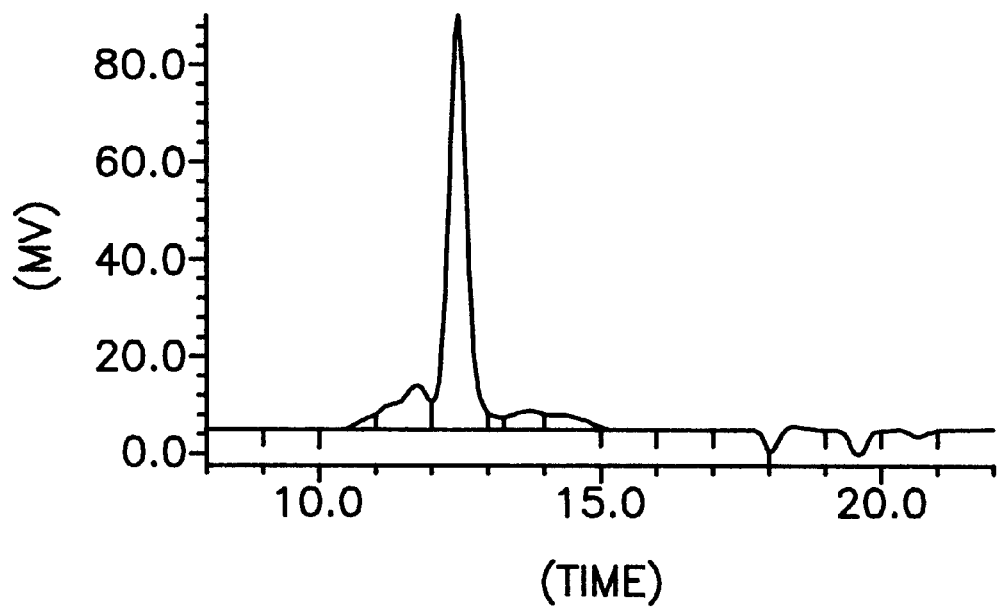
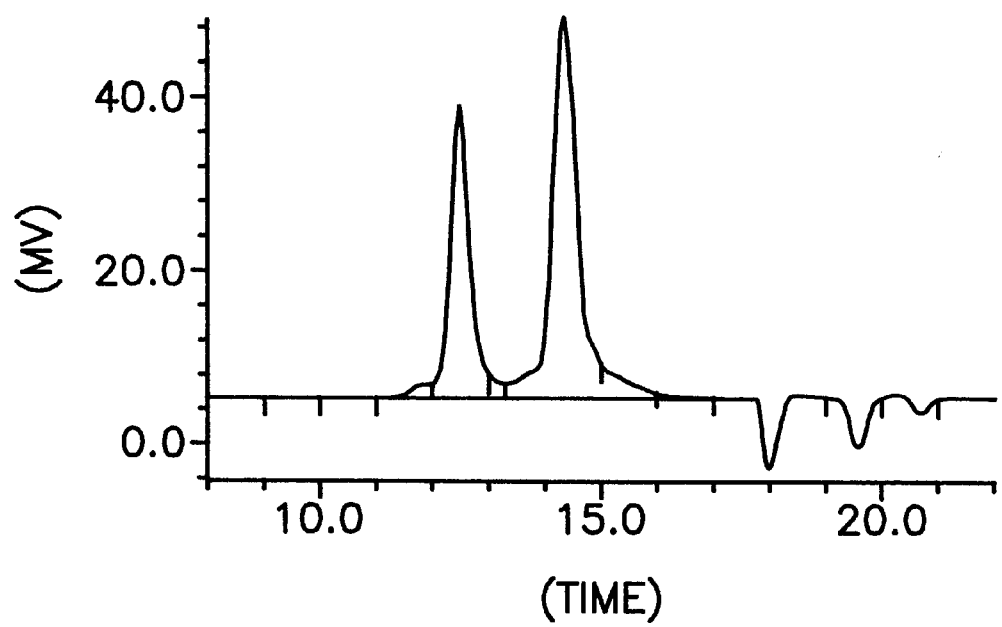

PRODUCTION OF BITUMINOUS EMULSION AND LIQUID AMINE EMULSIFIER THEREFOR

This application is the national phase under 35 U.S.C. §371 of prior PCT International Application No. PCT/JP96/02881 which has an International filing date of Oct. 3, 1996 which designated the United States of America, the entire contents of which are hereby incorporated by reference.

FIELD OF THE INVENTION

The present invention relates to a liquid amine compound which can be applied to various uses such as emulsification for bitumens since it has as high of a surface activity as solid amines and has a much better workability as compared with the solid amines, and to uses of the above compound thereby to emulsify the bitumens.

Further, the present invention provides a process for producing an emulsifier for bitumens, in which an acid is added to a liquid amine compound obtained by reacting a specific aliphatic amine with a carbonyl compound to adjust the pH so as to be not more than 5.

DESCRIPTION OF THE RELATED ART

In cationic surfactants used as emulsifiers for bitumens, hydrochlorides of aliphatic amines have so far been used in the form of an aqueous solution, and those having linear alkyl groups having 12 to 22 carbon atoms have been known as industrially useful ones. Since these amine compounds have long linear alkyl groups, they are solid or pasty at room temperatures and difficult to handle when using them.

Efforts for liquefying these amine compounds have so far been made but they have involved the following problems.

For example, a method for oxyalkylating alkylamines and alkylpropylenediamines, described in U.S. Pat. No. 2,930,701 and French Patent 1,462,981, and a method for methylating secondary nitrogen, disclosed in U.S. Pat. No. 4,561,900, sacrifice considerably the interface active characteristics. That is, in various applications, more addition amounts are required as compared with those of raw material solid amines, or in the case of making use of them for a purpose of preparing emulsions, more greater mechanical energy is needed.

Further, it can be considered to dilute them into liquids by organic solvents. In this case, however, it is difficult to raise the amine concentration to 60% or higher even with the use of lower alcohols having the largest dissolution power, and therefore the considerably large amounts of the organic solvents have to be blended. In this case, it is apparent that the evaporation of the organic solvents exerts an adverse effect on the environment, and the adverse effects of the organic solvents may be exerted on the performances according to the use.

Further, it is described in U.S. Pat. No. 4,701,484 to use the reaction products of organic amine compounds primarily with unsaturated aldehydes (acrolein and the like) as aldehyde compounds as an anti-stripping additive (an agent for increasing an adhesion between aggregates and asphalt in a hot mix composition) for heated asphalt. However, the above reaction products are nothing but disclosed as the anti-stripping agent for heated asphalt, and descriptions in terms of emulsification of bitumens are not found at all.

SUMMARY OF THE INVENTION

Intensive investigations made by the present inventors in order to solve the problems described above have resulted in finding that the reaction of an aliphatic amine having at least one hydrocarbon group having not less than 8 carbon atoms with a carbonyl compound can liquefy the amine compound without damaging the interface activity and that this liquid amine compound is excellent as a component for an emulsifier for bitumens, and thus coming to complete the present invention.

That is, the present invention relates to use of a liquid amine compound prepared by reacting an aliphatic amine having at least one hydrocarbon group having not less than 8 carbon atoms with a carbonyl compound for an emulsifier of bitumens.

Further, the present invention relates to use of a liquid amine composition prepared by adding at least one compound selected from the group consisting of (a) organic acids, (b) alcohols and (c) phenols to a liquid amine compound prepared by reacting the aliphatic amine having at least one hydrocarbon group having not less than 8 carbon atoms with a carbonyl compound for an emulsifier of bitumens.

The present invention relates to a liquid amine compound for emulsifying bitumens which is prepared by reacting an aliphatic amine having at least one hydrocarbon group having not less than 8 carbon atoms with a carbonyl compound.

Further, the present invention provides use of the liquid amine compound for an emulsifier of bitumens in water, and an emulsion composition comprising the liquid amine compound described above, a bitumen and water.

That is, the present invention relates to a process for producing an emulsifier for producing a bituminous emulsion, wherein an acid is added to the liquid amine compound for an emulsifier of bitumens to adjust the pH of the aqueous solution so as to be not more than 5.

Further, the present invention relates to a process for producing a bituminous emulsion composition, in which to a mixture comprising 50 to 80 wt % of bitumen and 50 to 20 wt % of water is added 0.05 to 10.0 wt % per the mixture of a liquid amine compound, which amine compound has been prepared by reacting an aliphatic amine having at least one hydrocarbon group having not less than 8 of carbon atoms and a carbonyl compound, and then an acid is added thereto to adjust the pH of the obtainable emulsion so as to be not more than 5 for controlling the equivalent ratio of the composition.

Also, the present invention relates to a liquid amine mixture comprising an aliphatic poly-amine having at least one hydrocarbon group having not less than 8 carbon atoms and a carbonyl compound.

Further, the present invention relates to a liquid amine compound prepared by reacting an aliphatic amine obtained by mixing an aliphatic mono-amine having at least one hydrocarbon group having not less than 8 carbon atoms with an aliphatic poly-amine having at least one hydrocarbon group having not less than 8 carbon atoms with a carbonyl compound.

Further, the present invention relates to a liquid amine composition prepared by adding at least one compound selected from the group consisting of (a) organic acids, (b) alcohols and (c) phenols to the prescribed amine compound.

DETAILED DESCRIPTION OF THE INVENTION

The liquid amine compound of the present invention, a production process of an emulsifier for producing a bituminous emulsion using the liquid amine compound, and a production process for a bituminous emulsion using the emulsifier will be described below in detail.

In producing the liquid amine compound of the present invention, an aliphatic amine (hereinafter referred to as the raw material amine) having at least one hydrocarbon group having not less than 8 carbon atoms is reacted with a carbonyl compound in the following conditions.

The reaction temperature is preferred to be in the range from the melting point of the raw material amine to about 200° C., more preferably 50 to 150° C. High temperatures exceeding 200° C. are not preferred since the raw material amine is deteriorated. On the other hand, at temperatures being lower than the melting point of the raw material amine, the raw material amine is in the state of solid so that the uniform reaction is not obtained.

The carbonyl compound used in the present invention can be used in the form of an aqueous solution. When the carbonyl compound is liquid, it can be used as it is. In the present invention, the reaction can be carried out by a method in which these liquids are dropwise added little by little to the molten raw material amine maintained at prescribed temperatures. This is because the reaction is a exothermic reaction, therefore, it is needed to facilitate temperature control. Accordingly, it is advantageous to add dropwise either of the raw material amine and the carbonyl compound over a some period of time, for example, preferably over a period of 0.1 to 5 hours. The raw material amine may be added dropwise to the carbonyl compound. Further, the raw material amine which has been molten by heating and the carbonyl compound can be fed at the same time into a reactor maintained at prescribed temperatures to react them continuously. In such a continuous process, the feed rates of the raw materials can be controlled so that the retention time of the reaction is 0.1 to 5 hours in order to complete the reaction.

In a batch system reaction, the reaction liquid is aged for further about 1 to 5 hours after finishing dropwise adding in order to complete the reaction. The aging temperatures may be the same as or higher than the temperature in dropwise adding.

Further, it is preferred to carry out a dehydration after aging in order to remove out water remaining in the reaction mixture. This is because when water remains in the product, the water is gradually separated during storage, and the product may unfavorably become heterogeneous. The dehydration may be carried out at temperatures elevated up to 100° C. or higher or may be carried out at temperatures of 100° C. or lower under reduced pressure. In the continuous process, the dehydration can be achieved by feeding the reaction mixture into a distillation column maintained at such temperatures and pressure. The product can be maintained homogeneously even when water remains in some cases according to the kind of the raw material amine, and therefore the dehydration is not needed.

A charge mole ratio of the carbonyl compound to the amine is preferably 0.1 to 10 times mole, more preferably 1.0 to 2.0 times mole. The mole ratio of less than 0.1 time mole reduces a fluidity-providing effect to the amines, which is the effect of the present invention. Meanwhile, the charge mole ratio exceeding 10 times mole does not further increase the effect.

The carbonyl compound used in the present invention includes aldehydes having 1 to 18 carbon atoms, preferably 1 to 10 carbon atoms and ketones having 3 to 8 carbon atoms.

As examples of the aldehyde having 1 to 18 carbon atoms, aliphatic aldehydes such as formaldehyde, acetaldehyde, glyoxal, propanal, n-butylaldehyde, isobutylaldehyde, crotonaldehyde, pentanal, hexanal, ethylbutylaldehyde, heptanal, octanal, 2-ethylhexylaldehyde, pelargonaldehyde, caprinic aldehyde, undecylaldehyde, lauraldehyde, tridecylaldehyde, myristaldehyde, pentadecylaldehyde, palmitaldehyde, margaraldehyde and stearic aldehyde; and heterocyclic aldehydes such as furfural can be cited. Further, paraformaldehyde can also be used as a raw material for formaldehyde. Among them, aldehydes having 1 to 10 carbon atoms, preferably 1 to 8 carbon atoms are preferred.

As examples of the ketone having 3 to 8 carbon atoms, aliphatic ketones such as acetone, methyl ethyl ketone, ethyl ketone, 1-pentanone, methyl propyl ketone, 2-hexanone, 3-hexanone, methyl isobutyl ketone, 1-heptanone, methylpentanone and octanone can be cited.

The aliphatic amine having at least one hydrocarbon group having 8 or more carbon atoms, which is the raw material amine used in the present invention includes the aliphatic amines represented by the following formula. Among them, the aliphatic amines having at least one linear hydrocarbon group having 8 to 22 carbon atoms are preferred.

(wherein, $R_1$ represents a linear hydrocarbon group having 8 to 22 carbon atoms; $R_2$ represents H or a linear hydrocarbon group having 8 to 22 carbon atoms; A represents an ethylene group or a propylene group; and p is a number of 0 to 4).

Specifically, the above aliphatic amines include monoamines such as decylamine, laurylamine, myristylamine, cetylamine, stearylamine, tallow amine and hydrogenated tallow amine; and diamines obtained by reacting them with acrylonitrile and hydrogenating thereof, for examples, N-aminopropyldecylamine, N-aminopropyllaurylamine, N-aminopropylmyristylamine, N-aminopropylcetylamine, N-aminopropylstearylamine, and N-aminopropyl tallow amine. Further, triamines and tetraamines into which amino nitrogens are introduced by repeating the same process can be given as the examples. They include, for example, triamines such as N-decyldipropylenetriamine, N-lauryldipropylenetriamine, N-myristyldipropylenetriamine, N-cetyldipropylenetriamine, N-stearyl-dipropylenetriamine and N-tallow alkyldipropylenetriamine; and tetraamines such as N-lauryltripropylenetetraamine, N-myristyltripropylenetetraamine, N-cetyltripropylenetetraamine, N-stearyltripropylenetetraamine and N-tallow alkyltripropylenetetraamine. They may be subjected to hydrogenation treatment by conventional methods after reacting with the carbonyl compound. In the present invention, among them, tallow amines, tallow poly-amines, hydrogenated tallow amines, and hydrogenated tallow poly-amines which are derived from beef tallow are preferred.

Particularly preferred aliphatic amine is at least one selected from the aliphatic mono-amine and the aliphatic poly-amine, a mixture of the aliphatic mono-amines and the aliphatic poly-amines, or at least one selected from the group consisting of tallow mono-amine, tallow poly-amine, hydrogenated tallow mono-amine, and hydrogenated tallow poly-amine which are derived from tallow, especially from beef tallow.

Further, the aliphatic amines represented by the formula described above in which $R_1$ or $R_2$ has preferably 10 to 22 carbon atoms, more preferably 12 to 22 carbon atoms, most preferably 16 to 18 carbon atoms.

In the present invention, the aliphatic amines described above can be used alone or in a mixture of two or more kinds thereof. When they are used in a mixture of two or more kinds thereof, the mixture preferably comprises the mono-amine and the poly-amine in terms of an emulsifying ability. When the mixture comprising the mono-amine and the poly-amine is used, a ratio of the mono-amine to the poly-amine is 10:90 to 60:40.

In the present invention, the reaction of the aliphatic amine having at least one hydrocarbon group having not less than 8 carbon atoms with the carbonyl compound is considered to be a nucleophilic addition reaction of amine nitrogen to a carbonyl carbon and a dehydration reaction following it.

The chemical structure of a product obtained by reacting a formaldehyde with the amine is considered to mainly comprise a dimer and a trimer which dimer and trimer are obtained by bonding intermolecularly nitrogens of the amine molecules via methylene bonds.

For example, in the case of a reaction of N-aminopropyl tallow alkylamine with formaldehyde, the following values were obtained as the analytical values of the product obtained in the reaction in which the charge mole ratio of formaldehyde to amine has been 1.5.

TABLE 1

|  | Raw material amine | Product |
| --- | --- | --- |
| Total amine value | 342 | 168 |
| Primary amine value | 187 | 16 |
| Secondary amine value | 147 | 11 |
| Tertiary amine value | 8 | 141 |

According to the above, bonding among amine nitrogens via methylene bonds reduces primary and secondary amines and markedly increases tertiary amines. It has been found that the amine molecules are methylene-bridged to be polymerized. Nitrogen turned into a Schiff base by the reaction of a primary amino group with aldehyde and methylene-bridged nitrogen have a very low basicity, and this results in a reduction in the total amine value of the product. The following values were obtained as the analytical values of the product obtained by the reaction of n-butylaldehyde with N-aminopropyl tallow alkylamine in an amount of 1.5 time mole per the amine.

TABLE 2

|  | Product |
| --- | --- |
| Total amine value | 295 |
| Primary amine value | 217 |
| Secondary amine value | 68 |
| Tertiary amine value | 10 |

In this case, the molecular weight was observed to merely increase only by a portion obtained by a condensation of n-butylaldehyde. The tertiary amine increased slightly, and dimerization and trimerization caused by condensation of the molecules scarcely took place. The resulting product was liquid.

Turbidity of a product is generated in some cases during storage of the product over a long period of time. In order to prevent this, at least one compound selected from the group consisting of (a) organic acids, (b) alcohols and (c) phenols in an amount of 1 to 20 wt % can be added to the aliphatic amine to be used in the reaction during or after producing the liquid amine. When the organic acids (a) and the phenols (c) are used, they are added preferably to a reaction mixture while producing the liquid amine, and in the case of the alcohols (b), they are added preferably to a reaction mixture after producing the liquid amine.

Preferable examples of the organic acids (a) include aliphatic carboxylic acids having 1 to 22 carbon atoms and are liquid at room temperatures, for example, formic acid, acetic acid, propionic acid, butyric acid, isobutyric acid, pentanoic acid, trimethylacetic acid, 2-methylbutanoic acid, 3-methylbutanoic acid, caproic acid, heptanoic acid, caprylic acid, pelargonic acid, 2-ethylhexanoic acid, isostearic acid, oleic acid, linoleic acid and linolenic acid. The organic acids having carbon atoms exceeding 22 are not preferred since they are solid at room temperatures and can be a factor of turbidity in some cases.

Preferable examples of the alcohols (b) include monohydric alcohols such as methyl alcohol, ethyl alcohol, isopropyl alcohol and oleyl alcohol; and polyhydric alcohols such as ethylene glycol, propylene glycol, glycerol, polyglycerol, diethylene glycol, polyethylene glycol and polypropylene glycol. Among them, polyhydric alcohols are preferred.

Preferable examples of the phenols (c) include phenol; alkylphenols such as cresol, 3,5-xylenol, nonylphenol, p-tert-butylphenol and isopropenylphenol; phenylphenol; resorcinol; catechol; hydroquinone; floroglucin, hydrolyzable tannins such as cashew nut husk liquid, gallnut, gall, smack, tara, varonia, myrobalan, oak (Kashiwa), divi-divi, algarobilla, laishtan and cascalote; condensed tannins such as gamvia, quebracho, mimosa, acacia, mangrove, hemlock, spruce, bilumaccachi, oak bark and persimmon tannin; degiputo, Chinese tannin, Turkish tannin, hamameli tannin, quebric acid tannin, ellagic acid tannin and refined tannic acids thereof; polyhydric phenols such as liqnin; and bisphenols such as bisphenol A, bisphenol F, bisphenol C and bisphenol E. Among them, polyhydric phenols are preferred.

According to the present invention, a cationic surfactant derived from the liquid amine compound and a bituminous emulsion composition containing the cationic surfactant as an essential component can be produced as well.

Turbidity present in the liquid amine compound obtained by reacting the amine compound with the carbonyl compound does not exert an adverse effect on an emulsifying ability in using the liquid amine compound as a cationic surfactant but causes the problem of bad appearance of the product in some cases. Pursuit of the cause of the turbidity has resulted in finding that non-amine components contained in the raw material amine are strongly related to it. In particular, among the non-amine components, amides having high solidifying points are liable to cause formation of the turbidity. It has been found that the liquid amine compound containing reduced turbidity matters or having no turbidity can be obtained by using the raw material amine containing less non-amine components.

The non-amine components are impurities contained in the amine compound, and the components which are not adsorbed on cation exchange resins are shown by weight percentage based on the weight of the sample.

Non-amine components derived from tallow fatty acids include amides such as myristic acid amide, palmitic acid amide, stearic acid amide, dimyristic acid amide, dipalmitic acid amide and distearic acid amide; and nitriles such as myristnitrile, palmitnitrile, and stearonitrile. Further, it is considered that a polymer of acrylonitrile and hydrocarbons used when the poly-amines are derived from the mono-amines are contained.

Results obtained by testing the effect of the turbidity caused by the non-amine components are shown in Table 3. The non-amine components are determined in the following manner:

Determination of non-amine component:

$5 \times 10^{-3}$ g equivalent of amine sample was dissolved in 200 ml of isopropanol and regenerated with a hydrochloric acid aqueous solution. Then, the solution was put into a 500 ml separating funnel together with 50 ml of cation exchange resins (Dowex 50 W×4, 50 to 100 mesh) which has been washed by isopropanol. The solution was shaken by means of a suitable shaking apparatus for about one hour to adsorb the amine components on the resins. After finishing shaking, the resin was filtered off, and isopropanol was distilled off from the filtrate. The non-adsorbed matters were weighed to determine a weight percentage thereof based on the weight of the sample.

TABLE 3

Influence of Non-amine component to Turbidity

| Kind of aldehydes (mole ratio) Raw material amine (non-amine component, wt %) | Amount of Turbid substance vol % (based on liquid amine) | | |
|---|---|---|---|
| | Propion- aldehyde (1.2) reactant | Isobutyl- aldehyde (1.5) reactant | Isobutyl- aldehyde (1.5) reactant + 2EH acid 5 wt %* |
| Hydrogenated tallow monoamine | | | |
| (0.7) | 1.6 | 2.0 | 0.0 |
| (0.4) | 5.0 | 8.0 | 0.8 |
| Tallow diamine | | | |
| (2.8) | 1.4 | 1.4 | 0.0 |
| (6.8) | 5.8 | 4.2 | 0.6 |
| Tallow triamine | | | |
| (4.7) | 2.5 | 1.2 | 0.0 |
| (9.6) | 4.0 | 4.8 | 0.4 |

*2-EH: 2-ethylhexanoic acid

As shown by Table 3, it can be found that the turbidity of the products can be reduced by using the raw material amines containing less non-amine components and that the turbidity can be overcome by adding a small amount of a branched acid (2-ethylhexanoic acid). In the present invention, the non-amine components contained in the aliphatic mono-amines reside preferably in an amount of not more than 1 wt %; the non-amine components contained in the aliphatic diamines reside preferably in an amount of not more than 5 wt %; and the non-amine components contained in the aliphatic triamines reside preferably in an amount of not more than 10 wt %. The non-amine components contained in the aliphatic tetramine or higher (amines in which p is 3 or more in the formula defined in above) reside preferably in the amount of not more than 10 wt %.

The liquid amine compound of the present invention is preferably used as a component for an asphalt emulsifier for road paving, roofing and water-proofing for revetment, and a component for anti-solidification agents for fertilizers and collectors for floatations.

When the liquid amine compound of the present invention is used for an emulsifier for bitumens, the liquid amine compound can be used as well in a mixture with other liquid amine compounds. The other liquid amine compounds include conventional liquid amine compounds. Among them, liquid poly-amine compounds are preferred. Further, the liquid poly-amine compounds include preferably poly-amine compounds having at least one unsaturated hydrocarbon group having 12 to 22 carbon atoms, liquid amine compounds derived from tall oil, and liquid poly-amine compounds obtained by adding alkylene oxide to aliphatic poly-amines having at least one straight or branched hydrocarbon group having 12 to 22 carbon atoms. A blend ratio of the liquid amine compound of the present invention to the other liquid amine compounds falls in a range of 10 to 60 wt %, preferably 30 to 50 wt % in terms of a content of the liquid amine compound according to the present invention.

Next, the bituminous emulsion composition of the present invention and a production process therefor will be explained.

The liquid amine compound of the present invention can be used as a cationic surfactant for emulsifying bitumens in the forms of acid salts of hydrochloric acid, perchloric acid, formic acid, acetic acid, monochloroacetic acid, nitric acid, sulfamic acid and methylsulfuric acid, or in the forms of quaternary ammonium salts using quaternizing agents such as dimethylsulfuric acid and methyl chloride. In this case, other surfactants can be used in combination.

The liquid amine compound of the present invention is decomposed into an acid salt of the raw material aliphatic amine and the carbonyl compound by deriving the liquid amine compound into the acid salt with hydrochloric acid or acetic acid and preparing an acid salt aqueous solution thereof (emulsifier). This decomposition ratio is varied according to an equivalent ratio of the acid, a concentration of the liquid amine compound contained in the aqueous solution, and the temperatures. The higher the decomposition ratio is, the better the emulsifying ability for the bituminous emulsion is, and the more stable emulsion is obtained.

Preferably, at least one compound selected from the group consisting of (a) organic acids, (b) alcohols and (c) phenols is added to the liquid amine compound, and an acid is further added thereto to adjust the pH of the aqueous solution so as to be not more than 5, whereby the emulsifier is obtained. Also preferably, a mixture comprising 50 to 80 wt % of a bitumen and 50 to 20 wt % of water to which the liquid amine compound described above is added in an amount of 0.05 to 10.0 wt % per the mixture, and an acid is added to adjust the pH of the resulting emulsion so as to be not more than 5, whereby the bituminous emulsion composition is produced.

More preferably, a mixture comprising 50 to 80 wt % of a bitumen and 50 to 20 wt % of water to which the liquid amine compound described above is added in an amount of 0.05 to 10.0 wt % per the mixture. Then, at least one compound selected from the group consisting of the organic acid (a), the alcohols (b) and the phenols (c) is added to the liquid amine compound, and an acid is added there to adjust the pH of the resulting emulsion so as to be not more than 5, whereby the bituminous emulsion composition is produced.

According to the above, the liquid amine compound of the present invention is preferably used after adjusting the pH of the derived acid salt aqueous solution so as to be not more than 5, preferably 0.1 to 4, more preferably 1.0 to 2.5. In this condition, the decomposition ratio is increased as compared with a condition where the pH exceeds 5, and therefore the higher emulsifying ability can be obtained.

The decomposition ratio at 25° C. in the case where the concentration of the hydrochloride is 0.7 wt % and the pH is adjusted to be 2.0 falls in a range of 60 to 98 wt %. The decomposition ratio can be obtained by determining the carbonyl compound produced in the aqueous solution.

The bituminous emulsion is a bituminous water-base emulsion obtained by emulsifying a bitumen with a emulsifier (surfactant).

The bitumen used in the present invention includes petroleum straight asphalt, semi-blown asphalt, cut-back asphalt, natural asphalt, petroleum tar, pitch, solvent-deasphalting asphalt, heavy oil, and a mixture of two or more kinds thereof.

Further, there can be used as well reformed asphalts blended with natural rubber, synthetic rubber such as styrene-butadiene copolymer and chloroprene copolymer, polymers such as polyethylene and ethylene-vinyl acetate copolymer, petroleum resins, and thermoplastic resins.

Surfactants to be used in combination in the present invention include the following ones.

Anionic surfactants include the following ones:
(I) formaldehyde condensation products of aromatic compounds such as naphthalene, alkylnaphthalene, alkylphenol and alkylbenzene with sulfonic acid or salts thereof; an average condensation degree of formaldehyde is preferably 1.2 to 100;
(II) formaldehyde condensation products of liqnosulfonic acid, liqnosulfonic acid salts, derivatives thereof, and aromatic compounds such as liqnosulfonic acid and naphthalene, and alkylnaphthalene with sulfonic acid, and salts of the formaldehyde condensation products; an average condensation degree of formaldehyde is preferably 1.2 to 50;

(III) polystyrenesulfonic acid or salts thereof, and copolymers of styrenesulfonic acid and other copolymerizable monomers, and salts thereof; the molecular weights are 500 to 500,000;

(IV) dicylopentadienesulfonic acid polymer or salts thereof; the molecular weights of the polymers are preferably 500 to 500,000;

(V) polyacrylic acid or salts thereof, and copolymers of acrylic acid and other copolymerizable monomers, and salts thereof; the molecular weights are preferably 500 to 500,000;

(VI) maleate of liquid polybutadiene; a molecular weight of the liquid polybutadiene is preferably 500 to 200,000;

(VII) copolymers of anhydrous maleic acid and/or anhydrous itaconic acid with other copolymerizable monomers; the molecular weights are preferably 500 to 500,000;

(VIII) the following anionic surfactants each having one or two hydrophilic groups in a molecule; (a) sulfuric acid ester salt of alcohol having 4 to 18 carbon atoms;

(b) alkane, alkene and/or alkylarylsulfonic acid having 4 to 18 carbon atoms, or salts thereof;

(c) sulfates or phosphates of alkyleneoxide adducts of compounds having at least one active hydrogen in a molecule, and salts thereof;

(d) sulfosuccinic acid salts which are esters of saturated or unsaturated fatty acids having 4 to 22 carbon atoms;

(e) alkyldiphenyl ether disulfonic acid or salts thereof; the alkyl group has 8 to 18 carbon atoms;

(f) rosinic acid or salts thereof; a mixed acid of rosinic acid and tall oil which is a mixed acid of higher fatty acids, and salts thereof;

(g) alkane or alkenefatty acids having 4 to 18 carbon atoms, and salts thereof;

(h) α-sulfofatty acid ester salt represented by the following formula:

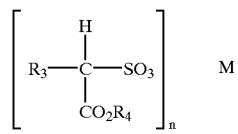

(wherein $R_3$ represents an alkyl group or alkenyl group having 6 to 22 carbon atoms; $R_4$ represents an alkyl group having 1 to 22 carbon atoms; M represents a monovalent or divalent metal atom, $NH_4$ or organic amine; and n is 1 or 2).

In the compounds (I) to (VIII), the salts include lower amines such as ammonium, monoethanolamine, diethanolamine, triethanolamine and triethylamine; and alkaline metals or alkaline earth metals such as sodium, potassium, magnesium and calcium.

The cationic surfactants include alkylamine salts, alkanolamine salts, quaternary ammonium salts, amine oxides and polyethylenepolyamines, and adducts of ethylene oxide and propylene oxide are included as well. In the case of the cationic surfactants which are not quaternary salts, they are used in the respective forms of acid salts of hydrochloric acid, acetic acid, nitric acid, sulfamic acid, and methylsulfuric acid.

The nonionic surfactants include polyethylene glycol type surfactants such as higher alcohol-ethylene oxide adducts, alkylenephenol-ethylene oxide adducts, fatty acid-ethylene oxide adducts, polyhydric alcohol-fatty acid ester-ethylene oxide adducts, higher alkylamine-ethylene oxide adducts, fatty acid amide-ethylene oxide adducts, oil or fat-ethylene oxide adducts and polypropylene glycol-ethylene oxide adducts; and polyhydric alcohol type surfactants such as fatty acid esters of glycerol, fatty acid esters of pentaerythritol, fatty acid esters of sorbitol and sorbitan, fatty acid esters of sucrose, polyalkylene glycol dialkyl esters, alkyl ethers of polyhydric alcohols, reaction products of alkylene oxide adducts and epoxy compounds, and fatty acid amides of alkanolamines.

The amphoteric surfactants include carboxylic acid salts of amino acid type and betaine type, sulfuric acid esters, sulfonic acid salts and phosphoric acid esters.

Further, water soluble inorganic salts such as ammonium chloride, calcium chloride, aluminum chloride, and iron chloride can be used in combination.

In addition to the above, polyhydric alcohols, polymer stabilizers and organic acids can be comprised as well. Any alcohols can be used as the polyhydric alcohols as long as they have at least 2 hydroxyl groups in a molecule and are soluble in water, for example, glycerol, polyglycerol, ethylene glycol, diethylene glycol, polyethylene glycol, propylene glycol, and monosaccharides and polysaccharides such as sorbitol and glucose.

Various water soluble polymers having molecular weights of 10,000 or more shown in Table 4 can be comprised as the polymer stabilizers.

Organic acids which are solid at room temperatures are preferred include, for example, aliphatic monohydric carboxylic acids such as undecylic acid, lauric acid, myristic acid, palmitic acid, stearic acid, hydroxystearic acid, arachidonic acid, behenic acid and erucic acid; aliphatic dihydric carboxylic acids such as oxalic acid, malonic acid, succinic acid, glutaric acid, adipic acid, pimelic acid, suberic acid, azelaic acid, sebacic acid and dimer acid; aromatic monohydric carboxylic acids such as benzoic acid, salicylic acid, p-hydroxybenzoic acid, toluic acid, aminobenzoic acid, sulfobenzoic acid, gallic acid, phenylacetic acid, mandelic acid, and phenylacrylic acid, phthalic acid, trimellitic acid, pyromellitic acid, and tannic acid.

TABLE 4

| Polymer stabilizer | |
|---|---|
| Water soluble synthetic polymer | Water soluble natural polymer |
| polyvinyl alcohol, sodium polyacrylic acid, polyacrylamide, polyvinyl pyrrolidone, polyvinyl methylether, polyvinyl sulfone, | Arabic gum, tragacanth gum, karaya gum, guar gum, tara gum, locust bean gum, tamarind gum, sodium alginate, alginic acid |

TABLE 4-continued

| Polymer stabilizer | |
|---|---|
| maleic acid copolymer, polyethylene oxide, polydiallylamine, polyethyleneimine Water soluble cellulose derivative | propyleneglycolester, carageenan, furcellaran, agar, high-methoxy pectin, low-methoxy pectin, chitin, chitosan |
| carboxymethyl cellulose, methyl cellulose, methylhydroxypropyl cellulose, hydroxyethyl cellulose, hydroxypropyl cellulose, other mixed ethers, sodium cellulose sulfuric acid ester | Fermentable polysaccharide xanthane gum, pulluran, cardran, dextran |
| Protein | Other |
| milk casein, sodium casein, gelatin, albumin, soy been casein | chondroitin sulfuric acid, hyaluronic acid |

A combined use ratio of the liquid amine compound of the present invention to the other surfactants is preferably 10 to 500 wt % of the other surfactants (including polyhydric alcohols and the polymer stabilizers) based on the liquid amine compound.

In the bituminous emulsion composition of the present invention, a blending ratio of the bitumen to water is preferably 50 to 80 wt % of the bitumen to 50 to 20 wt % of water. An addition amount of the liquid amine compound or liquid amine composition of the present invention is suitably 0.05 to 10.0 wt %, preferably 0.1 to 3.0 wt % based on the sum of the bitumen and water.

The bituminous emulsion composition can be prepared by preparing an aqueous solution of the surfactant described above and feeding the aqueous solution and an asphalt molten by heating into an emulsifying apparatus at the same time. An aqueous solution of the cationic surfactant of the present invention can be prepared by turning the liquid amine compound of the present invention into the form of hydrochloride or acetate.

The method for preparing the bituminous emulsion composition includes a method in which the liquid amine compound or composition of the present invention, water, an acid such as hydrochloric acid and acetic acid of an amount sufficient to adjust the pH of the aqueous solution so as to be not more than 5, preferably 1 to 4, and particularly preferably 1.0 to 2.5 in blending later, and asphalt molten by heating are fed into an emulsifying apparatus at the same time to prepare the bituminous emulsion composition (first method), a method in which an aqueous solution of the liquid amine compound or composition of the present invention is prepared, and the aqueous solution, an acid such as hydrochloric acid and acetic acid of an amount sufficient to adjust the pH of the aqueous solution so as to be not more than 5, preferably 1 to 4, and particularly preferably 1.0 to 2.5, and an asphalt molten by heating are fed into an emulsifying apparatus at the same time to prepare the bituminous emulsion composition (second method), and a method in which an aqueous solution of the liquid amine compound or liquid amine composition of the present invention, which is turned into the form of hydrochloride or acetate, wherein the pH is adjusted to be not more than 5, preferably 1 to 4, and particularly preferably 1.0 to 2.5, and an asphalt molten by heating are fed into an emulsifying apparatus at the same time to prepare the bituminous emulsion composition (third method). These aqueous solutions are used by heating at 25 to 98° C., preferably 40 to 70° C. The temperatures falling out of this range increase an asphalt particle diameter of the resulting emulsion and exert an adverse effect on the storage stability in some cases.

In general, temperatures for heating the asphalt are varied according to the penetration, and the asphalt having a smaller penetration has to be heated at higher temperatures. For example, the asphalt having a penetration of 80 to 100 can be used by heating at 130 to 150° C.

In the three methods described above, the respective components can be preblended before feeding into an emulsifying apparatus.

The emulsifying apparatus capable of being used in the present invention includes emulsifying apparatus and dispersing machines such as a homomixer, a homogenizer, a line mixer, a colloid mill, a sand mill, a milder, and a motionless mixer.

A shear rate in emulsifying is preferably 5,000 to 200,000 $s^{-1}$, more preferably 20,000 to 80,000 $s^{-1}$. The lower shear rate provides the emulsion composition having a larger asphalt particle diameter and causes a problem on a storage stability. Meanwhile, the shear rate which is increased too much can not provide the fine particle diameter and merely increases an energy consumption.

EXAMPLES

The present invention will now be explained in detail with reference to the examples shown below but the present invention is not be limited by these examples.

Example 1

200 g of tallow alkylpropylenediamine (total amine value: 342 mg KOH/g) was weighed to feed into a 1 liter four neck flask and heated to 65° C. 99.0 g of 37% formalin aqueous solution was dropwise added over a period of 3 hours. After aging at the same temperature for one hour, dehydration was carried out. The final condition of the dehydration was 75° C./50 mm Hg. The resulting reaction product showed fluidity at room temperatures. An analysis thereof resulted in showing that the total amine value was 165 mg KOH/g and the solidification temperature was 8° C. The solidification temperature was determined by evaluating the fluidity by every 1° C. in accordance with JIS K 2269. The infrared absorption spectra of the tallow alkylpropylenediamine and the resulting reaction product are shown in FIG. 1, the H-NMR spectra of the tallow alkylpropylenediamine and the resulting reaction product are shown in FIG. 2; and the analytical results of the resulting reaction product determined by GPC are shown in FIG. 3. The measuring conditions of GPC are as follows:

[Measuring conditions of GPC]
Column filler: styrene-divinylbenzene copolymer G2000 HXL+G1000 HXL (mfd. by Toso Co., Ltd.) (inner diameter: 7.8 mm and length: 30 cm in common)
Eluate: tetrahydrofuran
Detecting element: RI

Example 2

The amine compound obtained in Example 1 was subjected to hydrogenation treatment. The hydrogenation was carried out with a Raney nickel catalyst at a temperature of 130° C., 15 kg and for 2 hours. An analysis of the resulting product showed that the total amine value was 320.4 mg KOH/g and the solidification temperature was 9° C.

Example 3

200 g of tallow alkylpropylenediamine (total amine value: 342 mg KOH/g) was weighed to feed into a 1 liter four neck flask and heated to 65° C. 49.4 g of 37% formalin aqueous solution was dropwise added over a period of 2 hours. After aging at the same temperature for one hour, dehydration was carried out. The final condition of the dehydration was 75° C./50 mm Hg. The resulting reaction product showed fluidity at room temperatures, and an analysis thereof resulted in showing that the total amine value was 190.2 mg KOH/g and the solidification temperature was 10° C. The analytical results of the resulting reaction product determined by GPC are shown in FIG. 4.

Example 4

320 g of tallow alkyldipropylenetriamine (total amine value: 426 mg KOH/g) was weighed to feed into a 1 liter four neck flask and heated to 85° C. 98.5 g of 37% formalin aqueous solution was dropwise added over a period of 2 hours. After aging at the same temperature for one hour, dehydration was carried out. The final condition of the dehydration was 85° C./50 mm Hg. The resulting reaction product showed fluidity at room temperatures, and an analysis thereof resulted in showing that the total amine value was 311.0 mg KOH/g and the solidification temperature was 9° C.

Example 5

200 g of tallow alkyltripropylenetetraamine (total amine value: 485 mg KOH/g) was weighed into a 1 liter four neck flask and heated to 60° C. 87.6 g of 37% formalin aqueous solution was dropwise added over a period of 2 hours. After aging at the same temperature for 2 hours, dehydration was carried out. The final condition of the dehydration was 75° C./40 mm Hg. The resulting reaction product showed fluidity at room temperatures, and an analysis thereof resulted in showing that the total amine value was 293.6 mg KOH/g and the solidification temperature was 5° C.

Example 6

350 g of tallow alkyltripropylenetetramine (total amine value: 485 mg KOH/g) was weighed to feed into a 1 liter four neck flask and heated to 60° C. 42.9 g of 37% formalin aqueous solution was dropwise added over a period of 2 hours. After aging at the same temperature for 2 hours, dehydration was carried out. The final condition of the dehydration was 75° C./50 mm Hg. The resulting reaction product showed fluidity at room temperatures, and an analysis thereof resulted in showing that the total amine value was 353.6 mg KOH/g and the solidification temperature was 7° C.

Example 7

400 g of tallow alkyltripropylenetetraamine (total amine value: 485 mg KOH/g) was weighed to feed into a 1 liter four neck flask and heated to 65° C. 71.6 g of 80% acetaldehyde aqueous solution was dropwise added over a period of 2 hours. After aging at the same temperature for 2 hours, dehydration was carried out. The final condition of the dehydration was 80° C./50 mm Hg. The resulting reaction product showed fluidity at room temperatures, and an analysis thereof resulted in showing that the total amine value was 343.6 mg KOH/g and the solidification temperature was 6° C.

Example 8

200 g of stearylethylenediamine (total amine value: 342 mg KOH/g) was weighed to feed into a 1 liter four neck flask and heated to 80° C. 90.6 g of n-butylaldehyde was dropwise added over a period of 2 hours. After aging at the same temperature for 2 hours, dehydration was carried out. The final condition of the dehydration was 80° C./40 mm Hg. The resulting reaction product showed fluidity at room temperatures, and an analysis thereof resulted in showing that the total amine value was 283.4 mg KOH/g and the solidification temperature was 5° C.

Example 9

1.6 wt % of isostearic acid was added to the amine compound synthesized in Example 3, and the mixture was stirred at 60° C. for 30 minutes. This blended product had a solidification temperature of 10° C.

Example 10

2.5 wt % of 2-ethylhexanoic acid was added to the amine compound synthesized in Example 4, and the mixture was stirred at 60° C. for 30 minutes. This blended product had a solidification temperature of 8° C.

Example 11

3.5 wt % of 2-ethylhexanoic acid was added to the amine compound synthesized in Example 6, and the mixture was stirred at 60° C. for 30 minutes. This blended product had a solidification temperature of 6° C.

Example 12

200 g of tallow alkylmonoamine (total amine value: 214 mg KOH/g) was weighed to feed into a 1 liter four neck flask and heated to 65° C. 92.6 g of paraformaldehyde was charged dividing almost equally into four portions, and after completing charging, the reaction was continued at 65° C. for 2 hours. Dehydration was carried out with the final condition of 75° C./50 mm Hg to obtain a reaction product having a total amine value of 178 mg KOH/g and a solidification temperature of 10° C.

Example 13

360 g of tallow alkylpropylenediamine (total amine value: 342 mg KOH/g) was weighed to feed into a 1 liter four neck flask and heated to 65° C. 128 g of acetone was dropwise added over a period of one hour, and the mixture was aged at 65° C. for 2 hours. Dehydration was carried out with the final condition of 75° C./50 mm Hg to obtain a reaction product having a total amine value of 322 mg KOH/g and a solidification temperature of 4° C.

Example 14

250 g of tallow alkylpropylenediamine (total amine value: 342 mg KOH/g) was weighed to feed into a 1 liter four neck flask and heated to 95° C. 66 g of methyl ethyl ketone was dropwise added over a period of one hour, and the solution was aged at 95° C. for 2 hours. Dehydration was carried out in the final condition of 95° C./50 mm Hg to obtain a reaction product having a total amine value of 330 mg KOH/g and a solidification temperature of 4° C.

The charged mole ratios of the raw material amines to the carbonyl compounds in Examples 1 to 14 are shown in Table 5.

TABLE 5

|  | Kind of raw material | Mole ratio |
|---|---|---|
| Ex. 1 | Formaldehyde/tallow alkylpropylenediamine | 2.0 |
| Ex. 2 | Formaldehyde/tallow alkylpropylenediamine | 2.0 |
| Ex. 3 | Formaldehyde/tallow alkylpropylenediamine | 1.0 |
| Ex. 4 | Formaldehyde/tallow alkyldipropylenetriamine | 1.5 |
| Ex. 5 | Formaldehyde/tallow alkyltripropylenetetraamine | 2.5 |
| Ex. 6 | Formaldehyde/tallow alkyltripropylenetetraamine | 0.7 |
| Ex. 7 | Acetaldehyde/tallow alkyltripropylenetetraamine | 1.5 |
| Ex. 8 | n-Butylaldehyde/stearyl-ethylenediamine | 2.0 |
| Ex. 9 | Formaldehyde/tallow alkylpropylenediamine | 1.0 |
| Ex. 10 | Formaldehyde/tallow alkylpropylenetriamine | 1.5 |
| Ex. 11 | Formaldehyde/tallow alkyltripropylenetetraamine | 0.7 |
| Ex. 12 | Paraformaldehyde/tallow alkylmonoamine | 1.5 |
| Ex. 13 | Acetone/tallow alkylpropylenediamine | 2.0 |
| Ex. 14 | Methyl ethyl ketone/tallow alkylpropylenediamine | 1.2 |

[Evaluation of Interface Activity]

Hydrochloride aqueous solutions of the amine compounds prepared in Examples 1 to 9 and 12 to 14 and various amines prepared in Comparative Examples 1 to 4 shown below were prepared to determine interfacial tensions with oil. A pH of all solutions was adjusted as to be 3. The oil used was prepared by blending straight asphalt (penetration: 80 to 100) with gas oil No. 1 (JIS K 2204) in a weight ratio of 50/50. The interfacial tension was determined by a spinning drop method and calculated by the following equation:

$$\gamma = 0.552 \Delta\rho \times h^3 / f^2$$

γ: interfacial tension dyne/cm
Δρ: density difference g/cm³
h : width of oil droplet mm
f : rotation speed millisecond/rotation The measuring results are shown in Table 6.

TABLE 6

|  | Interfacial tension dyne/cm | | |
|---|---|---|---|
|  | 40° C.* | 60° C.* | 80° C.* |
| Example 1 | 2.82 | 2.40 | 2.20 |
| Example 2 | 2.92 | 2.50 | 2.30 |
| Example 3 | 2.10 | 1.80 | 1.50 |
| Example 4 | 2.50 | 2.30 | 2.10 |
| Example 5 | 2.92 | 2.42 | 2.26 |
| Example 6 | 2.03 | 1.70 | 1.42 |
| Example 7 | 2.02 | 1.90 | 1.65 |
| Example 8 | 2.40 | 2.15 | 1.95 |
| Example 9 | 2.84 | 2.41 | 2.22 |
| Example 12 | 3.09 | 2.85 | 2.65 |
| Example 13 | 2.56 | 2.40 | 2.30 |
| Example 14 | 2.76 | 2.58 | 2.42 |
| Comparative Example 1 | 6.25 | 5.30 | 4.90 |
| Comparative Example 2 | 4.10 | 3.80 | 3.40 |
| Comparative Example 3 | 3.50 | 3.20 | 2.90 |
| Comparative Example 4 | 3.74 | 3.45 | 3.10 |

*temperatures for measuring the interfacial tensions
Note:
Comparative Example 1: tallow alkylaminopropylamine-ethylene oxide 10 moles adduct
Comparative Example 2: 1-stearoxy-2-aminopropoxyethylene
Comparative Example 3: oleylaminopropylamine
Comparative Example 4: tallow alkyltripropylenetetraamine-ethylene oxide 4 moles adduct It can be found that the compounds of the present invention provide low interfacial tensions and have excellent interface activities as compared with those of the comparative compounds.

[Evaluation as Asphalt Emulsifier]

The compound of the present invention can be used as a component for an asphalt emulsifier used for road paving, roofing and water-proofing for revetment. Next, the examples thereof will be shown.

Aqueous solutions of the amine compounds prepared in Examples 1 to 14 and various amines prepared in Comparative Examples 1 to 4 described above were prepared in the forms of hydrochlorides. 415 g of the aqueous solution was heated to 50° C. and fed into a harrel type homogenizer at the same time as 600 g of straight asphalt having a penetration of 60 to 80, which had been molten by heating to 140° C., whereby an asphalt emulsion was produced. An addition amount of the surfactant was 0.3 wt % based on the sum of water and the asphalt. The emulsion was used to determine an asphalt particle diameter, an evaporation residual content, a viscosity, a sieve residual content, and a storage stability. These tests were carried out in accordance with ASTM D244-86. The results thereof are shown in Table 7.

Details on methods for determining the asphalt particle diameter, the evaporation residual content, the viscosity, the sieve residual content and the storage stability will be described below.

Measuring method for asphalt particle diameter:

Determined by a laser scattering particle analyzer (LA700, mfd. by Horiba Seisakusho Co. Ltd.).

Measuring method for evaporation residual content (%):

00±1 g of asphalt emulsion sample 3 was weighed into a prescribed vessel and heated on an electric heater for 20 to 30 minutes while stirring. The sample was further heated at 160° C. for one minute after it was confirmed that no water has been left. Then, the sample was left to stand for cooling down to room temperatures, and a residue (g) on evaporation was weighed. A percentage of the residue on evaporation based on the sample was determined to obtain an evaporation residual content (%).

Measuring method for sieve residual content (%):

A 1.18 mm net sieve having a depth of about 20 mm and a diameter of about 75 mm and a pan (metallic or ceramic) having a diameter of about 100 mm were precisely weighed by up to 0.5 g. The sieve is wetted in distilled water. 500±5 g of asphalt emulsion sample was weighed to feed into a beaker and poured on the sieve. The sieve was sufficiently washed with distilled water until an emulsion color of the residue on the sieve has been lost. Further, distilled water used for washing the beaker was poured as well on the sieve. The sieve was placed on the pan and put into a thermostatic bath of 110° C. to dry the sieve for 2 hours. After leaving to stand the sieve for cooling down to room temperatures, the whole weight of the sieve is weighed. The sieve residual content (%) was calculated by the following equation, and the value thus obtained was rounded to the first decimal place.

$$R = \frac{M3 - M2}{M1} \times 100$$

R : sieve residual content (%)

M1: weight (g) of the sample

M2: total weight (g) of sieve and pan

M3: total weight (g) of residue, sieve and pan

Evaluation Method for Storage Stability:

250 ml of asphalt emulsion produced was put into a prescribed cylinder and left for standing at a temperature of about 20° C. for 5 days. About 50 g of each sample was taken out of drawing ports in upper and lower parts of the cylinder to determine evaporation residual content (%). The storage stability was evaluated by a difference in the evaporation residual contents in the upper and lower parts. The smaller the difference is, the more stable and better the emulsion is.

Further, the amine compounds obtained in Examples 1, 3 and 7 were used in combination with the other surfactants shown in Table 8 to similarly evaluate them as the asphalt emulsifiers. The results thereof are shown in Table 8.

TABLE 7

| Kind of emulsifier | Particle diameter μm | Evaporation residual content wt % | viscosity* (25° C.) Saybolt sec* | Sieve residual content wt % | Storage stability 5 days Δ% |
|---|---|---|---|---|---|
| Ex. 1 | 3.4 | 62.6 | 22 | 0.1 | 3.3 |
| Ex. 2 | 3.6 | 61.6 | 20 | 0.0 | 3.9 |
| Ex. 3 | 2.8 | 61.0 | 22 | 0.1 | 2.0 |
| Ex. 4 | 2.9 | 63.5 | 24 | 0.0 | 2.2 |
| Ex. 5 | 4.2 | 62.3 | 22 | 0.2 | 4.0 |
| Ex. 6 | 3.7 | 62.2 | 22 | 0.1 | 3.5 |
| Ex. 7 | 3.5 | 62.9 | 23 | 0.0 | 2.1 |
| Ex. 8 | 4.0 | 62.8 | 22 | 0.1 | 4.1 |
| Ex. 9 | 3.2 | 61.9 | 21 | 0.1 | 3.0 |
| Ex. 10 | 3.1 | 62.0 | 22 | 0.1 | 2.2 |
| Ex. 11 | 3.5 | 61.5 | 22 | 0.1 | 2.9 |
| Ex. 12 | 4.5 | 62.1 | 20 | 0.2 | 3.9 |
| Ex. 13 | 3.8 | 61.8 | 21 | 0.2 | 3.4 |
| Ex. 14 | 3.6 | 62.5 | 20 | 0.1 | 3.1 |
| Comp. Ex. 1 | 5.8 | 62.0 | 19 | 0.8 | 8.6 |
| Comp. Ex. 2 | 5.6 | 62.7 | 19 | 0.4 | 10.2 |
| Comp. Ex. 3 | 7.4 | 63.4 | 18 | 1.6 | 16.1 |
| Comp. Ex. 4 | 6.5 | 63.2 | 19 | 0.7 | 11.5 |
| Comp. Ex. 5 | 6.8 | 63.1 | 22 | 0.5 | 12.3 |
| Comp. Ex. 6 | 10.2 | 61.8 | 18 | 2.8 | 35.6 |

*Value (flow time) determined by means of a Saybolt viscometer
Note:
Comparative Example 5: nonylphenol-ethylene oxide 20 moles adduct
Comparative Example 6: sodium stearylsulfate

TABLE 8

| Kind of emulsifier (wt %) | Other surfactant (wt %) | Evaporation residual content wt % | Sieve residual content wt % | Storage stability 5 days Δ% |
|---|---|---|---|---|
| Ex. 1 (0.25) | Ca lignosulfate (0.15) | 61.5 | 0.1 | 2.8 |
| Ex. 3 (0.25) | Stearylamine-ethylene oxide 4 moles adduct (0.10) | 60.9 | 0.2 | 2.6 |
| Ex. 3 (0.35) | Polyethylene glycol (0.08) (molecular wt: 800) | 61.5 | 0.1 | 1.8 |
| Ex. 7 (0.20) | Methyl cellulose (0.10) (molecular wt: 10,000) | 62.8 | 0.1 | 1.5 |

It can be found from the test results shown above that the compounds of the present invention can provide cationic surfactants which are improved in handling easiness that they are liquid at room temperatures while maintaining excellent emulsifying abilities.

Examples 15 to 21

200 g of hydrogenated tallow alkylpropylenediamine (total amine value: 341 mg KOH/g) was weighed to feed into a 1 liter four neck flask and heated to 65° C. 65.6 g of isobutylaldehyde and organic acids of kinds and amounts shown in Table 9 were dropwise added over a period of 2 hours. After aging at the same temperature for one hour, dehydration was carried out. The final condition of the dehydration was 75° C./50 mm Hg. Then, the reaction mixture was cooled down to 60° C., and alcohols of kinds and amounts shown in Table 9 were added to blend.

TABLE 9

| Ex. | Kind of organic acid | Addition amount (g) | Kind of alcohol | Addition amount (g) |
|---|---|---|---|---|
| 15 | No addition | 0 | No addition | 0 |
| 16 | 2-Ethylhexanoic acid | 12 | No addition | 0 |
| 17 | No addition | 0 | Polyethylene glycol (average molecular weight: 200) | 4 |
| 18 | 2-Ethylhexanoic acid | 12 | Polyethylene glycol (average molecular weight: 200) | 4 |
| 19 | 2-Ethylhexanoic acid | 20 | Glycerol | 2 |
| 20 | Caprylic acid | 10 | Polyglycerol | 12 |
| 21 | Heptanoic acid | 2 | Polypropylene glycol; triol type (average molecular weight 300) | 30 |

Examples 22 to 28

200 g of hydrogenated tallow alkylpropylenediamine (total amine value: 340 mg KOH/g) was weighed to feed into a 1 liter four neck flask and heated to 65° C. 98.3 g of 2-ethylhexylaldehyde was dropwise added thereto over a period of 2 hours. After aging at the same temperature for one hour, dehydration was carried out. The final condition of the dehydration was 75° C./50 mm Hg. Then, the reaction mixture was cooled down to 60° C., and organic acids and alcohols of kinds and amounts shown in Table 10 were added to blend.

TABLE 10

| Ex. | Kind of organic acid | Addition amount (g) | kind of alcohol | Addition amount (g) |
|---|---|---|---|---|
| 22 | 2-Ethylhexanoic acid | 12 | No addition | 0 |
| 23 | No addition | 0 | Glycerol | 4 |
| 24 | 2-Ethylhexanoic acid | 30 | Polyethylene glycol (average molecular weight 400) | 8 |
| 25 | 2-Ethylhexanoic acid | 12 | Glycerol | 4 |
| 26 | Caproic acid | 4 | Polyglycerol | 12 |
| 27 | Pentanoic acid | 8 | Ethylene glycol | 4 |
| 28 | Isobutyric acid | 2 | Propylene glycol | 20 |

[Evaluation as Asphalt Emulsifier]

The emulsifiers obtained in Examples 15 to 28 described above and the emulsifiers obtained in Comparative Examples 7 to 10 shown below were measured for solidification temperatures and presence of turbidity. The results thereof are shown in Table 11. The presence of turbidity was determined in the following manner.

Measurement of the presence of turbidity

The presence of turbidity of the respective amines was determined by visual observation after the storage (with naked eyes) at 15° C. for one month.

Next, aqueous solutions of the amine compounds obtained in Examples 15 to 28 and various amines obtained in Comparative Examples 7 to 10 described above were prepared in the forms of hydrochlorides. 415 g of the aqueous solution was heated to 50° C. and fed into a harrel type homogenizer at the same time as 600 g of straight asphalt having a penetration of 60 to 80, which had been molten by heating to 140° C., whereby an asphalt emulsion was produced. An addition amount of the surfactant was 0.3 wt % based on the sum of water and the asphalt. The emulsion was used to determine an asphalt particle diameter, an evaporation residual content, a viscosity, a sieve residual content, and a storage stability. These tests were carried out in accordance with ASTM D244-86. The results thereof are shown in Table 11.

TABLE 11

| Kind of emulsifier | Solidification temperature (°C.) | Presence of turbidity | Particle diameter μm | Evaporation residual content wt % | Viscosity (25° C.) Saybolt sec | Sieve residual content wt % | Storage stability 5 days Δ |
|---|---|---|---|---|---|---|---|
| Ex. 15 | −6 | Present | 3.3 | 61.2 | 22 | 0.1 | 3.3 |
| Ex. 16 | −7 | None | 2.8 | 61.8 | 21 | 0.1 | 3.2 |
| Ex. 17 | −6 | None | 2.9 | 61.7 | 20 | 0.0 | 3.2 |
| Ex. 18 | −7 | None | 3.1 | 62.7 | 20 | 0.1 | 3.0 |
| Ex. 19 | −5 | None | 3.7 | 61.1 | 22 | 0.2 | 3.7 |
| Ex. 20 | −6 | None | 3.5 | 60.8 | 21 | 0.1 | 3.9 |
| Ex. 21 | −7 | None | 3.3 | 61.2 | 20 | 0.0 | 4.1 |
| Ex. 22 | 3 | None | 3.9 | 62.2 | 22 | 0.1 | 2.2 |
| Ex. 23 | 3 | None | 4.1 | 62.0 | 22 | 0.1 | 2.5 |
| Ex. 24 | 2 | None | 3.9 | 61.8 | 23 | 0.2 | 4.6 |
| Ex. 25 | 2 | None | 4.2 | 61.8 | 22 | 0.1 | 3.1 |
| Ex. 26 | 2 | None | 3.8 | 61.7 | 20 | 0.1 | 3.8 |
| Ex. 27 | 3 | None | 3.7 | 61.9 | 21 | 0.2 | 3.2 |
| Ex. 28 | 1 | None | 3.8 | 62.1 | 21 | 0.1 | 3.8 |
| Comp. Ex. 7 | 0 | Present | 5.8 | 62.0 | 19 | 0.8 | 8.6 |
| Comp. Ex. 8 | 2 | Present | 5.6 | 62.7 | 19 | 0.4 | 10.2 |

TABLE 11-continued

| Kind of emulsifier | Solidification temperature (°C.) | Presence of turbidity | Particle diameter μm | Evaporation residual content wt % | Viscosity (25° C.) Saybolt sec | Sieve residual content wt % | Storage stability 5 days Δ |
|---|---|---|---|---|---|---|---|
| Comp. Ex. 9 | 0 | None | 7.4 | 63.4 | 19 | 1.6 | 16.0 |
| Comp. Ex. 10 | 15 | None | 6.5 | 63.2 | 19 | 0.7 | 11.5 |

Comparative Example 7: tallow alkylaminopropylamine-ethylene oxide 10 moles adduct
Comparative Example 8: 1-stearoxy-2-aminopropoxyethylene
Comparative Example 9: oleylaminopropylamine
Comparative Example 10: tallow alkyltripropylenetetraamine-ethylene oxide 4 moles adduct

[Evaluation of Emulsifying Ability by Difference in pH]

A similar experiment in which a pH of a hydrochloride aqueous solution prepared using the amine compound obtained in Example 16 was varied was carried out to evaluate an effect of pH exerted on a ability as an asphalt emulsifier. The results thereof are shown in Table 12.

TABLE 12

| pH | Evaporation residual content (wt %) | Sieve residual content (wt %) | Storage stability (5 days Δ%) |
|---|---|---|---|
| 0.8 | 60.6 | 0.1 | 2.2 |
| 2.0 | 61.6 | 0.0 | 3.9 |
| 3.2 | 60.9 | 0.3 | 4.4 |
| 4.5 | 61.1 | 0.8 | 8.3 |

It can be found from the test results shown above that the compounds of the present invention can provide emulsifiers for producing bituminous emulsions, which maintain excellent emulsifying abilities and are easy to handle and which are liquid at room temperatures.

Examples 29 to 64 and Comparative Examples 11 to 20

Synthetic compounds and comparative compounds shown below were used to carry out the following examples and comparative examples.

Synthetic Compound 1

200 g of hydrogenated tallow alkylmonoamine (total amine value: 215 mg KOH/g) was weighed to feed into a 1 liter four neck flask and heated to 65° C. 82.8 g of isobutylaldehyde was dropwise added over a period of 2 hours. After aging at the same temperature for one hour, dehydration was carried out. The final condition of the dehydration was 75° C./50 mm Hg. The resulting reaction product showed fluidity at room temperatures, and an analysis thereof resulted in showing that the total amine value was 187 mg KOH/g and the solidification temperature was 15° C.

Synthetic Compound 2

200 g of hydrogenated tallow alkylmonoamine (total amine value: 215 mg KOH/g) was weighed to feed into a 1 liter four neck flask and heated to 80° C. 141.0 g of lauraldehyde was dropwise added over a period of 2 hours. After aging at 85° C. for one hour, dehydration was carried out. The final condition of the dehydration was 85° C./30 mm Hg. The resulting reaction product showed fluidity at room temperatures, and an analysis thereof resulted in showing that the total amine value was 126 mg KOH/g and the solidification temperature was 9° C.

Synthetic Compound 3

141.0 g of tallow alkylpropylenediamine (total amine value: 341 mg KOH/g) 200 g was weighed to feed into a 1 liter four neck flask and heated to 65° C. 65.6 g of isobutylaldehyde was dropwise added over a period of 2 hours. After aging at the same temperature for one hour, dehydration was carried out. The final condition of the dehydration was 75° C./50 mm Hg. The resulting reaction product showed fluidity at room temperatures, and an analysis thereof resulted in showing that the total amine value was 288 mg KOH/g and the solidification temperature was -6° C.

Synthetic Compound 4

200 g of tallow alkyldipropylenetriamine (total amine value: 438 mg KOH/g) was weighed to feed into a 1 liter four neck flask and heated to 65° C. 56.2 g of isobutylaldehyde was dropwise added over a period of 2 hours. After aging at the same temperature for one hour, dehydration was carried out. The final condition of the dehydration was 75° C./50 mm Hg. The resulting reaction product showed fluidity at room temperatures, and an analysis thereof resulted in showing that the total amine value was 358 mg KOH/g and the solidification temperature was -6° C.

Synthetic Compound 5

60 g of hydrogenated tallow alkylmonoamine, 100 g of tallow alkylpropylenediamine and 40 g of tallow alkyldipropylenetriamine were weighed to feed into a 1 liter four neck flask and heated to 65° C. (total amine value: 323 mg KOH/g). 98.3 g of 37% formalin aqueous solution was dropwise added thereto over a period of 2 hours. After aging at the same temperature for one hour, dehydration was carried out. The final condition of the dehydration was 75° C./50 mm Hg. The resulting reaction product showed fluidity at room temperatures, and an analysis thereof resulted in showing that the total amine value was 196 mg KOH/g and the solidification temperature was 8° C.

Synthetic Compound 6

60 g of hydrogenated tallow alkylmonoamine, 100 g of tallow alkylpropylenediamine and 40 g of tallow alkyldipropylenetriamine were weighed to feed into a 1 liter four neck flask and heated to 65° C. (total amine value: 323 mg KOH/g). 59.2 g of 90% acetaldehyde aqueous solution was dropwise added thereto over a period of 2 hours. After aging at the same temperature for one hour, dehydration was carried out. The final condition of the dehydration was 75° C./50 mm Hg. The resulting reaction product showed fluidity at room temperatures, and an analysis thereof resulted in showing that the total amine value was 262 mg KOH/g and the solidification temperature was 15° C.

Synthetic Compound 7

60 g of hydrogenated tallow alkylmonoamine, 100 g of hydrogenated tallow alkylpropylenediamine and 40 g of hydrogenated tallow alkyldipropylenetriamine were weighed to feed into a 1 liter four neck flask and heated to 65° C. (total amine value: 318 mg KOH/g). 69.3 g of propionaldehyde was dropwise added over a period of 2 hours. After aging at the same temperature for one hour, dehydration was carried out. The final condition of the dehydration was 75° C./50 mm Hg. The resulting reaction product showed fluidity at room temperatures, and an analysis thereof resulted in showing that the total amine value was 255 mg KOH/g and the solidification temperature was 15° C.

Synthetic Compound 8

60 g of hydrogenated tallow alkylmonoamine, 100 g of tallow alkylpropylenediamine and 40 g tallow alkyldipropylenetriamine were weighed to feed into a 1 liter four neck flask and heated to 65° C. (total amine value: 323 mg KOH/g). 65.4 g of butylaldehyde was dropwise added over a period of 2 hours. After aging at the same temperature for one hour, dehydration was carried out. The final condition of the dehydration was 75° C./50 mm Hg. The resulting reaction product showed fluidity at room temperatures, and an analysis thereof resulted in showing that the total amine value was 250 mg KOH/g and the solidification temperature was 6° C.

Synthetic Compound 9

60 g of hydrogenated tallow alkylmonoamine, 100 g of hydrogenated tallow alkylpropylenediamine and 40 g of hydrogenated tallow alkyldipropylenetriamine were weighed to feed into a 1 liter four neck flask and heated to 65° C. (total amine value: 318 mg KOH/g). 64.5 g of isobutylaldehyde was dropwise added over a period of 2 hours. After aging at the same temperature for one hour, dehydration was carried out. The final condition of the dehydration was 75° C./50 mm Hg. The resulting reaction product showed fluidity at room temperatures, and an analysis thereof resulted in showing that the total amine value was 267 mg KOH/g and the solidification temperature was 10° C.

Synthetic Compound 10

60 g of hydrogenated tallow alkylmonoamine, 100 g of hydrogenated tallow alkylpropylenediamine and 40 g of hardened tallow alkyldipropylenetriamine were weighed to feed into a 1 liter four neck flask and heated to 85° C. (total amine value: 318 mg KOH/g). 95.0 g of benzaldehyde was dropwise added over a period of 2 hours. After aging at the same temperature for one hour, dehydration was carried out. The final condition of the dehydration was 85° C./50 mm Hg. The resulting reaction product showed fluidity at room temperatures, and an analysis thereof resulted in showing that the total amine value was 260 mg KOH/g and the solidification temperature was 5° C.

Synthetic Compound 11

60 g of hydrogenated tallow alkylmonoamine, 100 g of hydrogenated tallow alkylpropylenediamine and 40 g of hydrogenated tallow alkyldipropylenetriamine were weighed into a 1 liter four neck flask and heated to 85C (total amine value: 318 mg KOH/g). 61.2 g of 2-ethylhexylaldehyde was dropwise added over a period of 2 hours. After aging at the same temperature for one hour, dehydration was carried out. The final condition of the dehydration was 85° C./40 mm Hg. The resulting reaction product showed fluidity at room temperatures, and an analysis thereof resulted in showing that the total amine value was 236 mg KOH/g and the solidification temperature was 4° C.

Synthetic Compound 12

60 g of hydrogenated tallow alkylmonoamine, 100 g of tallow alkylpropylenediamine and 40 g of tallow alkyldipropylenetriamine were weighed to feed into a 1 liter four neck flask and heated to 65° C. (total amine value: 323 mg KOH/g). 111.6 g of lauraldehyde was dropwise added over a period of 2 hours. After aging at 80° C. for one hour, dehydration was carried out. The final condition of the dehydration was 85° C./30 mm Hg. The resulting reaction product showed fluidity at room temperatures, and an analysis thereof resulted in showing that the total amine value was 210 mg KOH/g and the solidification temperature was −3° C.

Synthetic Compound 13

60 g of hydrogenated tallow alkylmonoamine, 100 g of tallow alkylpropylenediamine and 40 g of tallow alkyldipropylenetriamine were weighed to feed into a 1 liter four neck flask and heated to 65° C. (total amine value: 323 mg KOH/g). 116.4 g of palmitaldehyde was dropwise added over a period of 2 hours. After aging at 80° C. for one hour, dehydration was carried out. The final condition of the dehydration was 85° C./30 mm Hg. The resulting reaction product showed fluidity at room temperatures, and an analysis thereof resulted in showing that the total amine value was 208 mg KOH/g and the solidification temperature was 5° C.

Synthetic Compound 14

60 g of hydrogenated tallow alkylmonoamine, 100 g of tallow alkylpropylenediamine and 40 g of tallow alkyldipropylenetriamine were weighed to feed into a 1 liter four neck flask and heated to 60° C. (total amine value: 323 mg KOH/g). 70.3 g of acetone was dropwise added over a period of 2 hours. After aging at the same temperature for one hour, dehydration was carried out. The final condition of the dehydration was 75° C./30 mm Hg. The resulting reaction product showed fluidity at room temperatures, and an analysis thereof resulted in showing that the total amine value was 265 mg KOH/g and the solidification temperature was 12° C.

Synthetic Compound 15

60 g of hydrogenated tallow alkylmonoamine, 100 g of hydrogenated tallow alkylpropylenediamine and 40 g of hydrogenated tallow alkyldipropylenetriamine were weighed to feed into a 1 liter four neck flask and heated to 60° C. (total amine value: 318 mg KOH/g). A mixture of 34.7 g of propionaldehyde and 43.0 g of isobutylaldedhyde was dropwise added over a period of 2 hours. After aging at the same temperature for one hour, dehydration was-carried out. The final condition of the dehydration was 75° C./50 mm Hg. The resulting reaction product showed fluidity at room temperatures, and an analysis thereof resulted in showing that the total amine value was 256 mg KOH/g and the solidification temperature was 12° C.

Synthetic Compound 16

60 g of stearylmonoamine, 100 g of stearylpropylenediamine and tallow 40 g of alkyltripropylenetetraamine were weighed to feed into a 1 liter four neck flask and heated to 65° C. (total amine value: 329 mg KOH/g). 66.4 g of isobutylaldehyde was dropwise added over a period of 2 hours. After aging at the same temperature for 2 hours, dehydration was carried out. The final condition of the dehydration was 80° C./40 mm Hg. The resulting reaction product showed fluidity at room temperatures, and an analysis thereof resulted in showing that the total amine value was 274 mg KOH/g and the solidification temperature was 9° C.

Synthetic Compound 17

60 g of hydrogenated tallow alkylmonoamine, 100 g of tallow alkylpropylenediamine and 40 g of tallow alkyldipropylenetriamine are weighed to feed into a 1 liter four neck flask and heated to 85° C. (total amine value: 323 mg KOH/g). 65.5 g of isobutylaldehyde was dropwise added over a period of 2 hours. After aging at the same temperature for one hour, dehydration was carried out. The final condition of the dehydration was 85° C./40 mm Hg. The resulting reaction product showed fluidity at room temperatures, and an analysis thereof resulted in showing that the total amine value was 267 mg KOH/g and the solidification temperature was 5° C.

Synthetic Compound 18

100 g of hydrogenated tallow alkylmonoamine, 80 g of tallow alkylpropylenediamine and 20 g of tallow alkyldipropylenetriamine were weighed to feed into a 1 liter four neck flask and heated to 80° C. (total amine value: 288 mg KOH/g). 69.4 g of isobutylaldehyde was dropwise added over a period of 2 hours. After aging at the same temperature for one hour, dehydration was carried out. The final condition of the dehydration was 85° C./40 mm Hg. The resulting reaction product showed fluidity at room temperatures, and an analysis thereof resulted in showing that the total amine value was 240 mg KOH/g and the solidification temperature was 8° C.

Synthetic Compound 19

40 g of hydrogenated tallow alkylmonoamine, 120 g of tallow alkylpropylenediamine and 40 g of tallow alkyldipropylenetriamine were weighed to feed into a 1 liter four neck flask and heated to 75° C. (total amine value: 335 mg KOH/g). 64.6 g of isobutylaldehyde was dropwise added over a period of 2 hours. After aging at the same temperature for one hour, dehydration was carried out. The final condition of the dehydration was 85° C./40 mm Hg. The resulting reaction product showed fluidity at room temperatures, and an analysis thereof resulted in showing that the total amine value was 280 mg KOH/g and the solidification temperature was 5° C.

Synthetic Compound 20

60 g of hydrogenated tallow alkylmonoamine and 140 g of tallow alkylpropylenediamine were weighed to feed into a 1 liter four neck flask and heated to 75° C. (total amine value: 303 mg KOH/g). 55.0 g of isobutylaldehyde was dropwise added over a period of 2 hours. After aging at the same temperature for one hour, dehydration was carried out. The final condition of the dehydration was 85° C./40 mm Hg. The resulting reaction product showed fluidity at room temperatures, and an analysis thereof resulted in showing that the total amine value was 258 mg KOH/g and the solidification temperature was 3° C.

Synthetic Compound 21

5.0 wt % of 2-ethylhexanoic acid and 1.5 wt % of PEG 200 based on the amine compound obtained in Synthetic Compound 17 were added the amine compound, and the components were mixed while stirring at 60° C. for 30 minutes. This mixture had a solidification temperature of 4° C.

Synthetic Compound 22

1.5 wt % of linoleic acid and 3.0 wt % of PEG 200 of based on the amine compound obtained in Synthetic Compound 17 were added to the amine compound, and the components were mixed while stirring at 60° C. for 30 minutes. This mixture had a solidification temperature of 5° C.

The raw material amines, aldehydes and the charge mole ratios are shown in Table 13. A ratio of the raw material amines is a weight ratio.

TABLE 13

| Synthetic Compound | Kind of raw material | Mole ratio |
|---|---|---|
| 1 | Isobutylaldehyde/hydrogenated tallow monoamine | 1.5 |
| 2 | Lauraldehyde/hydrogenated tallow monoamine | 1.0 |
| 3 | Isobutylaldehyde/tallow diamine | 1.5 |
| 4 | Isobutylaldehyde/tallow triamine | 1.5 |
| 5 | Formaldehyde/hydrogenated tallow monoamine:tallow diamine:tallow triamine = 3:5:2 | 2.0 |
| 6 | Acetaldehyde/hydrogenated tallow monoamine:tallow diamine:tallow triamine = 3:5:2 | 2.0 |
| 7 | Propionaldehyde/hydrogenated tallow monoamine:hydrogenated tallow diamine:hydrogenated tallow triamine = 3:5:2 | 2.0 |
| 8 | Butylaldehyde/hydrogenated tallow monoamine:tallow diamine:tallow triamine = 3:5:2 | 1.5 |
| 9 | Isobutylaldehyde/hydrogenated tallow monoamine:hydrogenated tallow diamine:hydrogenated tallow triamine = 3:5:2 | 1.5 |

TABLE 13-continued

| Synthetic Compound | Kind of raw material | Mole ratio |
|---|---|---|
| 10 | Benzaldehyde/hydrogenated tallow monoamine:hydrogenated tallow diamine:hydrogenated tallow triamine = 3:5:2 | 1.5 |
| 11 | 2-Ethylhexyaldehyde/hydrogenated tallow monoamine:hydrogenated tallow diamine:hydrogenated tallow triamine = 3:5:2 | 0.8 |
| 12 | Lauraldehyde/hydrogenated tallow monoamine:tallow diamine:tallow triamine = 3:5:2 | 1.0 |
| 13 | Palmitaldehyde/hydrogenated tallow monoamine:tallow diamine:tallow triamine = 3:5:2 | 0.8 |
| 14 | Acetone/hydrogenated tallow monoamine tallow diamine:tallow triamine = 3:5:2 | 2.0 |
| 15 | Propionaldehyde (1.0 mole) + isobutylaldehyde (1.0 mole)/hydrogenated tallow monoamine:hydrogenated tallow diamine:hydrogenated tallow triamine = 3:5:2 | 2.0 |
| 16 | Isobutylaldehyde/stearylmonoamine steatyldiamine:tallow tetraamine = 3:5:2 | 1.5 |
| 17 | Isobutylaldehyde/hydrogenated tallow monoamine:tallow diamine:tallow triamine = 3:5:2 | 1.5 |
| 18 | Isobutylaldehyde/hydrogenated tallow monoamine:tallow diamine:tallow triamine = 5:4:1 | 1.5 |
| 19 | Isobutylaldehyde/hydrogenated tallow monoamine:tallow diamine:tallow triamine = 2:6:2 | 1.5 |
| 20 | Isobutylaldehyde/hydrogenated tallow monoamine:tallow diamine = 3:7 | 1.2 |
| 21 | Isobutylaldehyde/hydrogenated monoamine:tallow diamine:tallow triamine = 3:5:2 | 1.5 |
| 22 | Isobutylaldehyde/hydrogenated monoamine:tallow diamine:tallow triamine = 3:5:2 | 1.5 |

[Evaluation as Asphalt Emulsifier]

The compound of the present invention can be used as a component for an asphalt emulsifier used for road paving, roofing and water-proofing for revetment. Next, the examples thereof shall be shown.

Aqueous solutions of the amine compounds prepared in Synthetic Compounds 1 to 22 and various amines prepared in Comparative Compounds 1 to 4 were prepared in the forms of hydrochlorides. 415 g of the aqueous solution was heated to 50° C. and fed into a harrel type homogenizer at the same time as 600 g of straight asphalt having a penetration of 60 to 80, which had been molten by heating to 140° C., whereby an asphalt emulsion was produced. An addition amount of the surfactant was 0.25 wt % based on the sum of water and the asphalt. The emulsion was used to determine an asphalt particle diameter, a storage stability and a viscosity. These tests were carried out in accordance with ASTM D244-86. The results thereof are shown in Tables 14 and 15.

TABLE 14

| | Kind of emulsifier | Particle diameter (μm) | Evaporation residual content (wt %) | Viscosity [25° C.] (Saybolt sec*) | Storage stability (5 days, Δ%) |
|---|---|---|---|---|---|
| Ex. 29 | Synthetic Compound 1/ Synthetic Compound 3 = 3/7 | 3.0 | 60.2 | 31 | 2.5 |
| Ex. 30 | Synthetic Compound 2/ Synthetic Compound 3 = 3/7 | 3.2 | 60.8 | 30 | 2.8 |
| Ex. 31 | Synthetic Compound 2/ Comparative Compound 1 = 3/7 | 4.0 | 60.9 | 26 | 3.5 |
| Ex. 32 | Synthetic Compound 2/ Comparative Compound 2 = 3/7 | 3.8 | 61.2 | 28 | 3.3 |
| Ex. 33 | Synthetic Compound 2/ Comparative Compound 3 = 3/7 | 3.4 | 60.5 | 29 | 3.0 |
| Ex. 34 | Synthetic Compound 1/ Synthetic Compound 3/ Synthetic Compound 4 = 3/5/2 | 2.9 | 61.2 | 33 | 2.1 |
| Ex. 35 | Synthetic Compound 5 | 4.8 | 61.5 | 22 | 4.2 |
| Ex. 36 | Synthetic Compound 6 | 3.1 | 60.5 | 33 | 2.4 |
| Ex. 37 | Synthetic Compound 7 | 3.6 | 61.1 | 36 | 0.8 |
| Ex. 38 | Synthetic Compound 8 | 3.2 | 60.7 | 31 | 2.3 |
| Ex. 39 | Synthetic Compound 9 | 2.8 | 60.8 | 38 | 0.6 |
| Ex. 40 | Synthetic Compound 10 | 3.0 | 61.0 | 65 | 1.0 |
| Ex. 41 | Synthetic Compound 11 | 3.4 | 60.9 | 33 | 1.0 |
| Ex. 42 | Synthetic Compound 12 | 3.9 | 60.6 | 27 | 3.9 |
| Ex. 43 | Synthetic Compound 13 | 4.2 | 60.4 | 26 | 4.1 |
| Ex. 44 | Synthetic Compound 14 | 3.3 | 61.3 | 32 | 2.6 |
| Ex. 45 | Synthetic Compound 15 | 3.4 | 60.8 | 38 | 0.8 |
| Ex. 46 | Synthetic Compound 16 | 3.0 | 61.2 | 30 | 1.2 |
| Ex. 47 | Synthetic Compound 17 | 2.7 | 61.0 | 27 | 2.4 |
| Ex. 48 | Synthetic Compound 18 | 5.1 | 61.5 | 35 | 2.0 |
| Ex. 49 | Synthetic Compound 19 | 2.5 | 60.9 | 23 | 2.6 |
| Ex. 50 | Synthetic Compound 20 | 2.9 | 61.9 | 32 | 2.2 |
| Ex. 51 | Synthetic Compound 21 | 2.8 | 61.3 | 26 | 2.6 |
| Ex. 52 | Synthetic Compound 22 | 2.8 | 60.8 | 27 | 2.5 |
| Ex. 53 | Synthetic Compound 3 | 5.4 | 61.2 | 18 | 8.3 |
| Comp. Ex. 11 | Comparative Compound 1 | 8.5 | 60.9 | 11 | 25.3 |
| Comp. Ex. 12 | Comparative Compound 2 | 7.8 | 61.4 | 13 | 19.7 |
| Comp. Ex. 13 | Comparative Compound 3 | 7.6 | 61.0 | 13 | 18.7 |
| Comp. Ex. 14 | Comparative Compound 4 | 8.0 | 62.0 | 12 | 20.2 |

*Value (flow time) determined by means of a Saybolt viscometer
Comparative Example 1: tallow alkylaminopropylamine-ethylene oxide 10 moles adduct
Comparative Example 2: 1-stearoxy-2-aminopropoxyethylene
Comparative Example 3: oleylaminopropylamine
Comparative Example 4: tallow alkyltripropylenetetraamine-ethylene oxide 4 moles adduct Further, the addition amounts of the amine compounds obtained in Synthetic Compounds 9 and 17 and Comparative Compounds 1 and 2 were varied to evaluate them as the asphalt emulsions. The results thereof are shown in Table 16.

TABLE 16

| | Kind of emulsifier | Addition amount of emulsifier % | Particle diameter μm | Evaporation residual content wt % | viscosity [25° C.] Saybolt sec | Sieve residual content wt % | Storage stability 5 days, Δ% |
|---|---|---|---|---|---|---|---|
| Ex. 54 | Synthetic Compound 9 | 0.25 | 2.8 | 60.8 | 38 | 0.0 | 0.6 |
| Ex. 55 | Synthetic Compound 9 | 0.20 | 4.5 | 60.2 | 27 | 0.0 | 0.8 |
| Ex. 56 | Synthetic Compound 9 | 0.15 | 5.8 | 61.4 | 23 | 0.0 | 1.9 |
| Ex. 57 | Synthetic Compound 9 | 0.125 | 6.8 | 61.1 | 19 | 0.0 | 3.8 |
| Ex. 58 | Synthetic Compound 17 | 0.25 | 2.7 | 61.0 | 27 | 0.0 | 2.4 |
| Ex. 59 | Synthetic Compound 17 | 0.20 | 3.7 | 60.8 | 21 | 0.0 | 2.6 |
| Ex. 60 | Synthetic Compound 17 | 0.15 | 5.1 | 61.2 | 19 | 0.0 | 2.9 |
| Comp. Ex. 15 | Comparative Compound 1 | 0.35 | 4.8 | 61.5 | 19 | 0.3 | 4.2 |

TABLE 16-continued

|  | Kind of emulsifier | Addition amount of emulsifier % | Particle diameter µm | Evaporation residual content wt % | viscosity [25° C.] Saybolt sec | Sieve residual content wt % | Storage stability 5 days, Δ% |
|---|---|---|---|---|---|---|---|
| Comp. Ex. 16 | Comparative Compound 1 | 0.30 | 6.2 | 62.0 | 16 | 0.5 | 9.6 |
| Comp. Ex. 17 | Comparative Compound 1 | 0.25 | 8.5 | 60.9 | 11 | 1.0 | 25.3 |
| Comp. Ex. 18 | Comparative Compound 2 | 0.35 | 4.8 | 61.5 | 22 | 0.0 | 3.9 |
| Comp. Ex. 19 | Comparative Compound 2 | 0.30 | 5.8 | 60.9 | 19 | 0.1 | 8.6 |
| Comp. Ex. 20 | Comparative Compound 2 | 0.25 | 7.8 | 61.4 | 13 | 0.2 | 19.7 |

The amine compounds obtained in Synthetic Compounds 7, 9 and 17 were used in combination with the other surfactants shown in Table 17 to evaluate them as asphalt emulsifiers. The results thereof are shown in Table 17.

TABLE 17

|  | Kind of emulsifier (wt %) | Other surfactant (wt %) | Evaporation residual content (wt %) | Sieve residual content (wt %) | Storage stability (5 days, Δ%) |
|---|---|---|---|---|---|
| Ex. 61 | Synthetic compound 7 (0.25) | Polycarboxylic acid (0.15) [molecular wt: 250,000] | 61.5 | 0.0 | 0.5 |
| Ex. 62 | Synthetic compound 9 (0.20) | Stearylamine-ethylene oxide 4 moles adduct (0.10) | 60.9 | 0.0 | 0.6 |
| Ex. 63 | Synthetic compound 9 (0.15) | Methyl cellulose (0.10) [molecular wt: 10,900] | 62.8 | 0.0 | 0.3 |
| Ex. 64 | Synthetic compound 17 (0.20) | Polyalkylene glycol distearyl ester (0.05) [molecular wt: 20,000] | 61.5 | 0.0 | 1.8 |

It can be found from the test results described above that the compounds of the present invention show emulsifying powers which are more excellent by twice or more than those of conventional liquid amines while maintaining liquidity at room temperatures.

Figure 1:
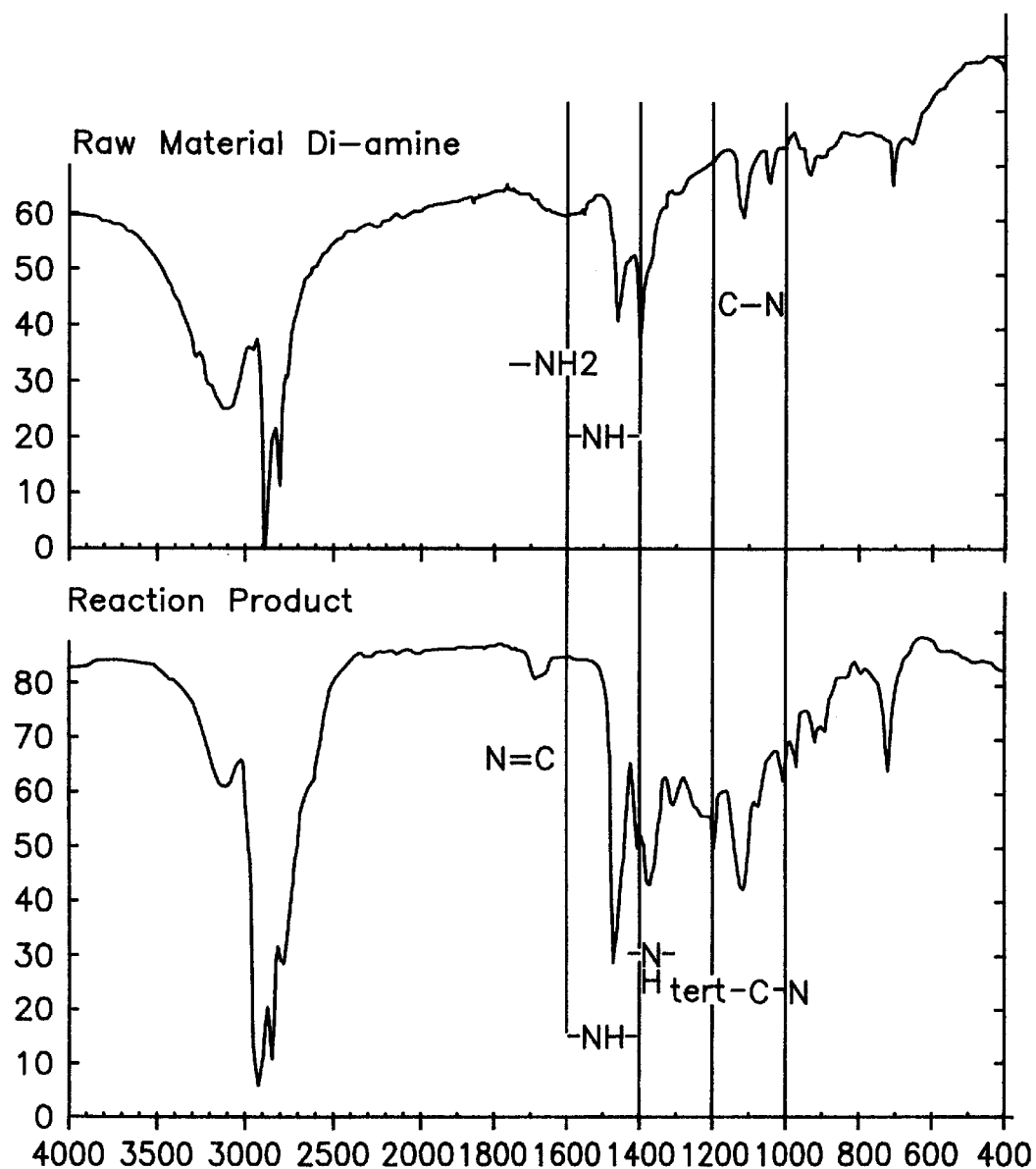
[FIG. 1]
Figure 2:
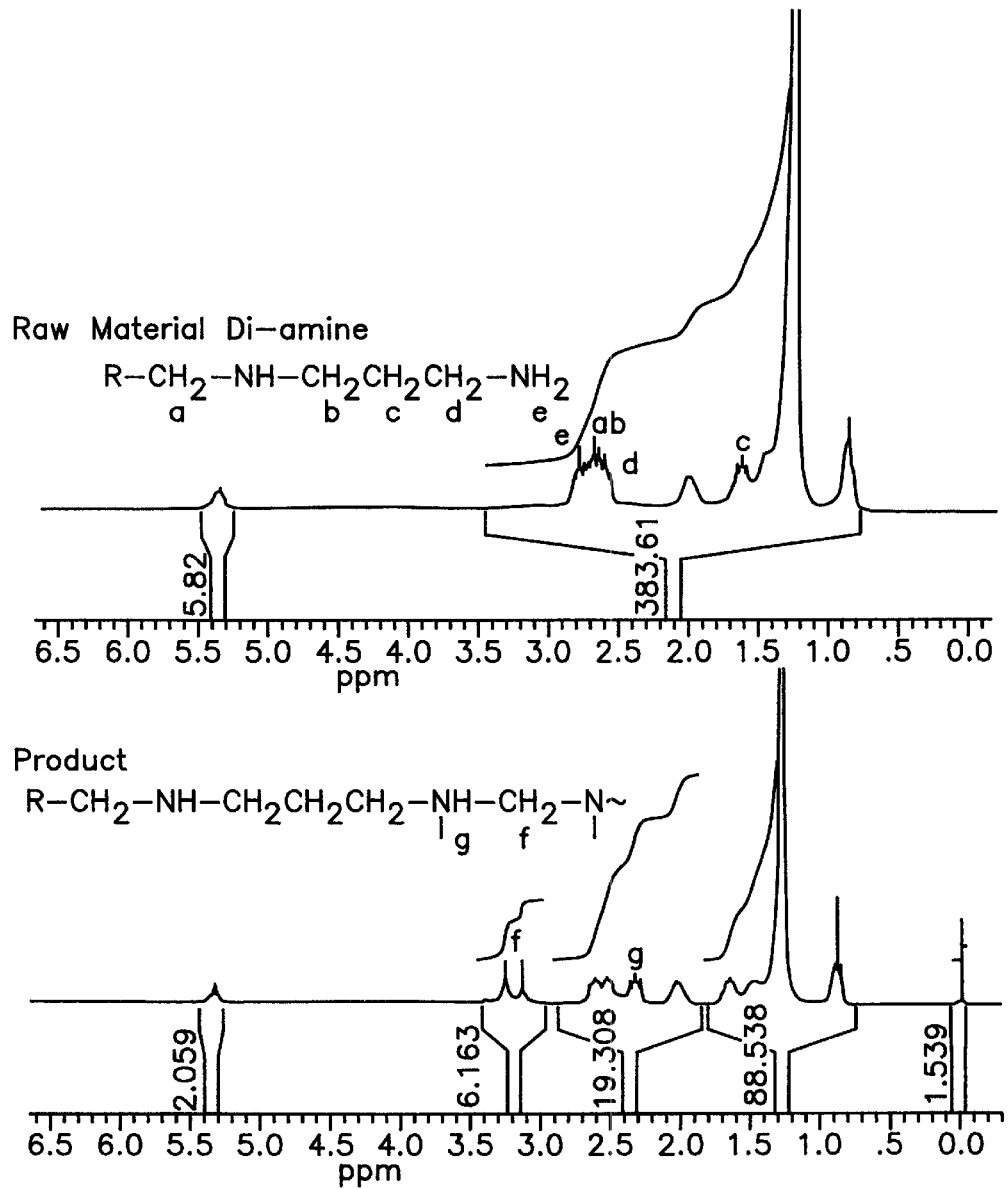

A diagram showing the infrared absorption spectra of the tallow alkylpropylenediamine used as a raw material diamine and the resulting reaction product in Example 1.

[FIG. 2]

A diagram showing the H-NMR spectra of the tallow alkylpropylenediamine used as a raw material diamine used and the resulting reaction product in Example 1.

[FIG. 3]

A diagram showing the analytical results of the reaction product obtained in Example 1 by means of GPC.

[FIG. 4]

A diagram showing the analytical results of the reaction product obtained in Example 3 by means of GPC.

We claim:

1. A method for emulsifying bitumens in water, comprising mixing bitumens and water in the presence of an acid and a liquid amine compound, wherein the liquid amine compound is prepared by reacting an aliphatic amine having at least one hydrocarbon group having not less than 8 carbon atoms with a carbonyl compound; and feeding the mixture and molten asphalt into an emulsifying apparatus wherein the emulsion obtained has a pH value of not more than 5.

2. The method of claim 1, wherein the aliphatic amine is at least one selected from the group consisting of an aliphatic mono-amine and an aliphatic poly-amine.

3. The method of claim 1, wherein the aliphatic amine is a tallow amine or a hydrogenated tallow amine.

4. The method of claim 1, wherein the aliphatic amine is an aliphatic mono-amine.

5. The method of claim 1, wherein the aliphatic amine is an aliphatic poly-amine.

6. The method of claim 1, wherein the aliphatic amine is a mixture of an aliphatic mono-amine and an aliphatic poly-amine.

7. The method of claim 1, wherein the aliphatic amine is selected from the group consisting of a tallow mono-amine, a tallow poly-amine, a hydrogenated tallow mono-amine and a hydrogenated tallow poly-amine.

8. The method of claim 1, wherein the carbonyl compound is an aldehyde having 1 to 18 carbon atoms.

9. The method of claim 1, wherein the carbonyl compound is an aliphatic aldehyde or a heterocyclic aldehyde, both having 1 to 10 carbon atoms.

10. The method of claim 1, wherein the carbonyl compound is a ketone having 3 to 8 carbon atoms.

11. A method according to claim 1, wherein the mixture comprises 50 to 80 wt % of bitumen, 50 to 20 wt % of water, and 0.05 to 10.0 wt % of the liquid amine compound.

12. The method as claimed in claim 11, further comprising adding to the mixture at least one compound selected from the group consisting of (a) organic acids, (b) alcohols and (c) phenols.

13. The method of claim 1, wherein the bitumens, water, the liquid amine compound and the acid are mixed together simultaneously.

14. The method of claim 1, wherein the water, the liquid amine compound, and the acid are mixed together, and then the resulting aqueous solution is mixed with the bitumens to be emulsified.

15. The method of claim 1, wherein the water, the liquid amine compound, and the acid are mixed together to form an acid salt of the liquid amine, and then the resulting aqueous solution is mixed with the bitumens to be emulsified.

16. The method of claim 1, wherein the aliphatic amine has at least one hydrocarbon group having 8 to 22 carbon atoms.

17. The method of claim 1, which further comprises mixing at least one compound selected from the group consisting of (a) organic acids, (b) alcohols and (c) phenols.

18. A process for producing an emulsifier by adding an acid to a liquid amine compound prepared by reacting an aliphatic amine having at least one hydrocarbon group having 8 to 22 carbon atoms with a carbonyl compound to adjust the pH of an aqueous solution so as to be not more than 5.

19. The process as claimed in claim 18, in which at least one compound selected from the group consisting of (a) organic acids, (b) alcohols and (c) phenols is further added to the liquid amine compound.

* * * * *

UNITED STATES PATENT AND TRADEMARK OFFICE
CERTIFICATE OF CORRECTION

PATENT NO. : 6,013,681
DATED : Jan. 11, 2000
INVENTOR(S) : Asamori et al.

It is certified that error appears in the above-indentified patent and that said Letters Patent is hereby corrected as shown below:

On the title page item [22], please change the filing date from "Oct. 6, 1996" to --Oct.3, 1996--.

Signed and Sealed this

Tenth Day of April, 2001

Attest:

NICHOLAS P. GODICI

Attesting Officer     Acting Director of the United States Patent and Trademark Office